(12) United States Patent
Llorens-Cortes et al.

(10) Patent No.: US 6,340,708 B1
(45) Date of Patent: Jan. 22, 2002

(54) PHARMACEUTICAL COMPOSITION COMPRISING AT LEAST ONE AMINOPEPTIDASE A INHIBITOR

(75) Inventors: Catherine Llorens-Cortes, Bures sur Yvette; Pierre Corvol, Paris; Marie-Claude Fournié-Zaluski, Paris; Bernard Pierre Roques, Paris, all of (FR)

(73) Assignees: Institut National de la Sante et de la Recherche Medicale (Inserm); Centre National de la Recherche Scientifique (C.N.R.S.), both of Paris (FR)

( * ) Notice: Subject to any disclaimer, the term of this patent is extended or adjusted under 35 U.S.C. 154(b) by 0 days.

(21) Appl. No.: 09/600,238
(22) PCT Filed: Jan. 14, 1999
(86) PCT No.: PCT/FR99/00059
    § 371 Date: Aug. 22, 2000
    § 102(e) Date: Aug. 22, 2000
(87) PCT Pub. No.: WO99/36066
    PCT Pub. Date: Jul. 22, 1999

(30) Foreign Application Priority Data

Jan. 16, 1998 (FR) ............................. 98 00453

(51) Int. Cl.⁷ ........................................... A61K 31/185
(52) U.S. Cl. ..................................................... 514/578
(58) Field of Search ......................................... 514/578

(56) References Cited

PUBLICATIONS

Chauvel et al (I), J. Med. Chem., vol 37, pp. 2950–2957, 1994.*
Zini et al, Proc. Natl. Acad. Sci., vol. 93, pp. 11968–11973, Oct. 1996.*
Chauvel et al (Il), J. Med. Chem., vol. 37, pp. 1339–1346, 1994.*
Ramirez et al, Regulatory Peptides, vol. 72, pp. 155–159, 1997.*
Ahmad et al, J. Prarmacol. Exp Ther., vol. 252, #2, pp. 643–650, 1990.*
Sullivan et al, Brian Research, vol. 456, #2, pp. 249–253, 1988.*
Appenrodt et al, Neuropeptides, vol. 26, pp. 175–180, 1994.*
Wright et la, J. of Hypertension, vol. 8, #10, pp. 969–974, 1990.*

* cited by examiner

Primary Examiner—James H. Reamer
(74) Attorney, Agent, or Firm—Larson & Taylor PLC

(57) ABSTRACT

The invention relates primarily to a pharmaceutical composition which can be used for lowering arterial blood pressure and is characterized in that it contains as active ingredient at least one selective aminopeptidase A inhibitor. Said inhibitor can notably be (S) 3-amino-4-mercaptobutyl sulfonic acid or one of its salts.

14 Claims, 8 Drawing Sheets

PHARMACEUTICAL COMPOSITION COMPRISING AT LEAST ONE AMINOPEPTIDASE A INHIBITOR

Figure 1:
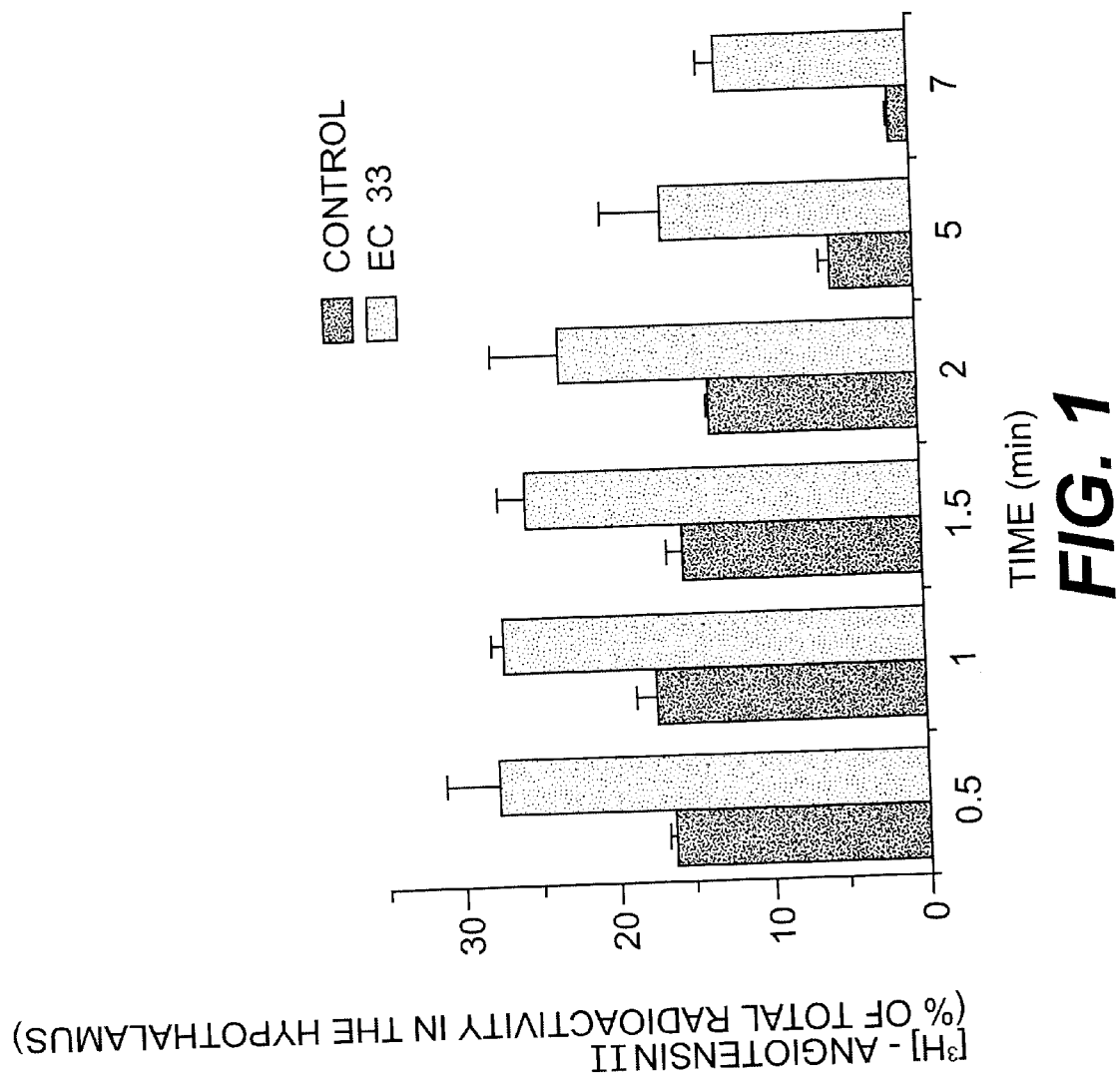

The present invention relates to a pharmaceutical composition which is useful in particular for treating disorders linked to an arterial hypertension.

Arterial hypertension is a disorder whose causes are still unknown. However, it is known that the central nervous system plays an important role in regulating the cardiovascular system by controlling both the activity of the autonomic sympathetic nervous system and of the baroreflex, as well as the release of hypophyseal hormones.

Similarly, clinical and experimental work suggests that the activity of the central nervous system and of the peripheral sympathetic nerves participates in the genesis of arterial hypertension.

It has also been shown that a renin/angiotensin system also exists in the central nervous system. It turns out that it controls cardiovascular functions and homeostasis of body fluids. All the components of the systemic renin/angiotensin system, including the precursors and enzymes required for angiotensin formation and degradation, as well as angiotensin receptors, have already been identified in the brain.

In the systemic renin/angiotensin system, it is known in particular that angiotensin II is generated under the action of an essentially membrane-bound enzyme which belongs to the zinc metalloprotease group. This ectopeptidase is known under the name of angiotensin converting enzyme (ACE) since it transforms the inactive peptide angiotensin I into angiotensin II.

It turns out that this angiotensin II is transformed in vivo into angiotensin III (AngIII) under the action of another zinc ectopeptidase, which has recently been cloned, aminopeptidase A (APA), which removes the N-terminal aspartyl residue of angiotensin II to result in angiotensin III. This angiotensin III is itself destroyed by various peptidases including in particular aminopeptidase N (APN).

These two zinc ectopeptidases, APA and APN, belong to the thermolysin-type enzyme group and have significant homology between their amino acid sequences.

It has been demonstrated that the inhibition of the enzyme for converting angiotensin I into angiotensin II, ACE, present in the systemic renin-angiotensin system leads, via a blockage of angiotensin II formation, to a drop in arterial pressure which is particularly sensitive in individuals suffering from hypertension. It turns out that these inhibitors block peripheral ACE both in the circulation and especially in many tissues: vascular endothelium, lung, kidney, etc.

Consequently, up until now it has been suggested that angiotensin II is the principal mediator of the cerebral renin-angiotensin system, by analogy with the peripheral system.

In fact, contrary to what has been accepted, it seems that in the cerebral renin/angiotensin system, the critical step is not thought to be the formation of angiotensin II by action of ACE on angiotensin I, but the formation of angiotensin III by action of APA on angiotensin II. This determinant role of angiotensin III in the cerebral renin/angiotensin system is in particular reinforced by the results which are shown in Example 4 below.

This set of data thus tends to identify angiotensin III as the effector peptide of the cerebral renin/angiotensin system, it being responsible for the increase in arterial pressure. More specifically, in the brain, it appears that Ang III exerts a tonic stimulatory effect on the central control of arterial pressure.

The present invention is based precisely on the demonstration that angiotensin III plays an essential role in controlling arterial pressure at the central level.

More particularly, the present invention is directed towards providing a pharmaceutical composition which makes it possible to decrease arterial pressure and thus to oppose an angiotensin III-induced increase in pressure.

More specifically, it claims a pharmaceutical composition which is useful for decreasing arterial pressure, characterized in that it comprises, as an active principle, at least one selective aminopeptidase A inhibitor.

As mentioned previously, aminopeptidase A (APA) is an ectoenzyme which belongs to the zinc metalloprotease family, the bacterial model of which is thermolysin.

APA is a glycoprotein which is in the form of a homodimer.

The cloning of its cDNA has revealed that each monomer is composed of an anchoring domain which separates a short N-terminal cytosolic segment from a large C-terminal extracellular domain which contains the active site including more particularly the zinc-binding site.

Now, it turns out that APA exhibits 34% amino acid sequence identity with APN, which itself is involved in the degradation of angiotensin III. This homology is, moreover, the highest at precisely the active site present in the glycosylated extracellular domain.

It is clear that this sequence homology between APA and APN constitutes a handicap for obtaining inhibitors which are specific and selective with regard to APA.

As mentioned above, the inhibitor used in the composition claimed is an inhibitor which is selective with regard to APA. This selectivity is revealed in particular by an affinity which is multiplied approximately by at least a factor of 100 for APA compared to APN.

More specifically, a molecule which is considered according to the invention to be an inhibitor which is selective with regard to APA, is a molecule which satisfies at least one of the following criteria:

its inhibitory potency on APA in vitro is less than or equal to $10^{-7}$ M, it exhibits a selectivity factor of approximately 100 with respect to the enzymes aminopeptidase N, aminopeptidase B (EC 3.4.11.6) and neutral endopeptidase (EC 3.4.24.11), and the angiotensin converting enzyme (EC 3.4.15.1).

when injected in vivo via the intracerebroventricular or systemic (if it crosses the blood-brain barrier) route, it blocks the formation of angiotensin III.

As an APA inhibitor which most particularly suits the invention, mention may be made in particular of (S)-3-amino-4-mercaptobutylsulphonic acid or a salt thereof with a pharmaceutically acceptable acid or base.

As emerges from the examples presented below, sodium (S)-3-amino-4-mercaptobutylsulphonate, hereafter referred to under the symbol EC33, exhibits significant inhibitory activity with regard to APA.

This inhibitor advantageously exhibits a selectivity factor of 100 with respect to aminopeptidase N.

When injected in mice via the intracerebroventricular route, in an amount of 30 µg, a significant increase is noted in the half-life of angiotensin II (30 µg), of a factor of about 2.6 compared to that observed in a control animal. In parallel, it totally blocks the formation of angiotensin III in the hypothalamus.

Similarly, experiments carried out in normotensive (WKY) or hypertensive (SHR) rats show that the injection of EC33 makes it possible to significantly decrease arterial pressure. The hypertensive effects of this APA inhibitor, EC33, is at a maximum for a dose of 100 µg. It is −22 mmHg in normotensive rats and −28 mmHg in hypertensive rats. The duration of action at this dose is on average between 40 and 60 minutes.

These results thus show that APA, the enzyme responsible for producing angiotensin III in the central nervous system, constitutes a novel therapeutic target of the cerebral renin/angiotensin system, and that the use of an APA inhibitor makes it possible to significantly reduce arterial pressure.

The pharmaceutical compositions claimed can optionally contain one or more pharmaceutically acceptable vehicles. These vehicles are chosen so as to constitute a pharmaceutical composition which can be administered conventionally via the oral, transmucous, parenteral or rectal route.

Their optimal methods of administration, doses and pharmaceutical forms can be determined according to the criteria generally taken into account in establishing a therapeutic treatment which is suited to a patient, such as for example the age or body weight of the patient, the seriousness of his general condition, the tolerance to the treatment and the observed side effects, etc.

Consequently, the compositions according to the invention are particularly advantageous for treating essential arterial hypertension during which the sympathetic hyperactivity often observed during the early phase is probably mediated by an increased activity of the cerebral renin/angiotensin system.

As non-limiting illustrations of the disorders which can be treated with the compositions claimed, mention may be made in particular of heart and kidney failures, hydrodynamic homeostasis disorders and proteinurea decrease in diabetics.

In addition, the compositions according to the invention can be advantageously used in addition to the blockers of the systemic renin/angiotensin system.

As representatives of these blockers, mention may be made in particular of converting enzyme inhibitors such as Enaprilate and angiotensin II receptor antagonists such as Losartan.

According to one variant of the invention, the composition claimed also comprises an angiotensin I converting enzyme inhibitor or an AT1 receptor antagonist.

This type of blocker of the systemic renin/angiotensin system proves to be effective in pathologies such as hypertension, congestive heart failure and left ventricular dysfunction after myocardial infarction, but also in improving proteinurea in diabetics and in reducing the progression of chronic kidney failure.

The compositions claimed will also be effective for treating the infections mentioned above, by also acting at the level of the central control of arterial pressure and by blocking the activity of the central renin/angiotensin system via their APA inhibitor.

The invention also extends to the use of an APA inhibitor as defined above combined, where appropriate, with a pharmaceutically acceptable vehicle for manufacturing a medicine which is useful for decreasing arterial pressure.

It can be in particular (S)-3-amino-4-mercaptobutylsulphonic acid or a pharmaceutically acceptable salt thereof with an acid or base.

FIGURES

FIG. 1: Evolution with time of the tritiated AngII content in murine hypothalamus in the presence or absence of EC33.

Figure 2:
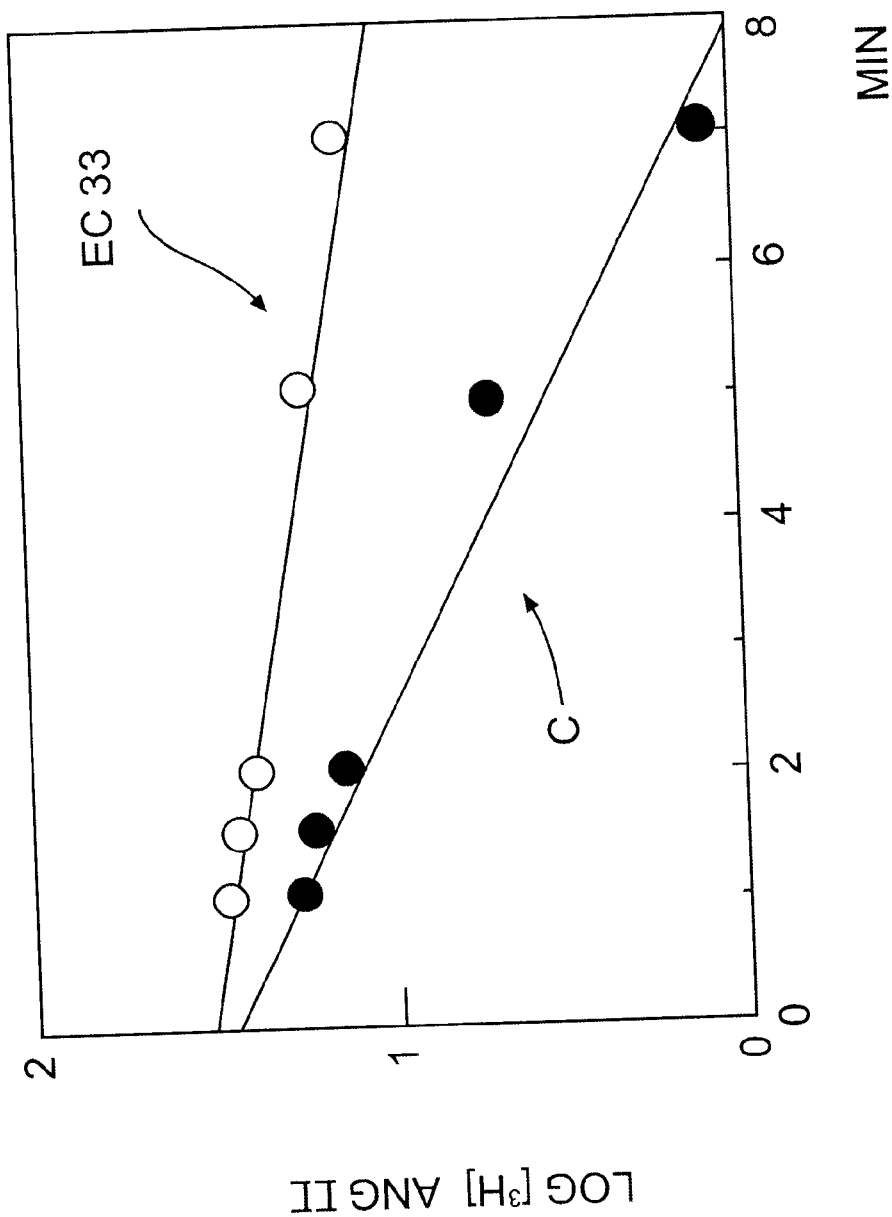

FIG. 2: Semi-logarithmic representation of the tritiated AngII contents in murine hypothalamus in the absence (control) or presence of EC33 (30 µg).

Figure 3:
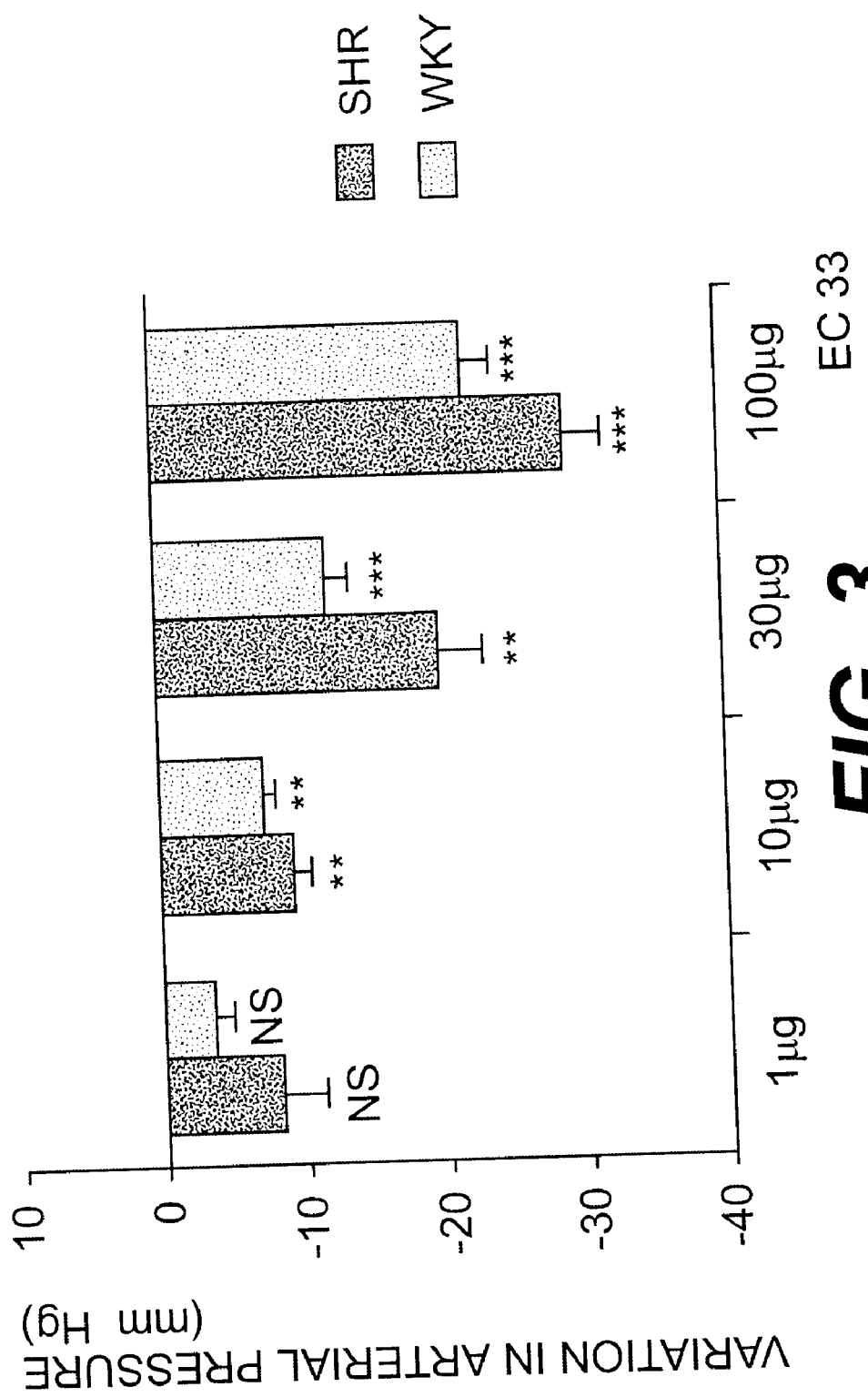

FIG. 3: Effect of various doses of EC33 injected via the intracerebroventricular route on arterial pressure in SHR and WKY rats.

Figure 4:
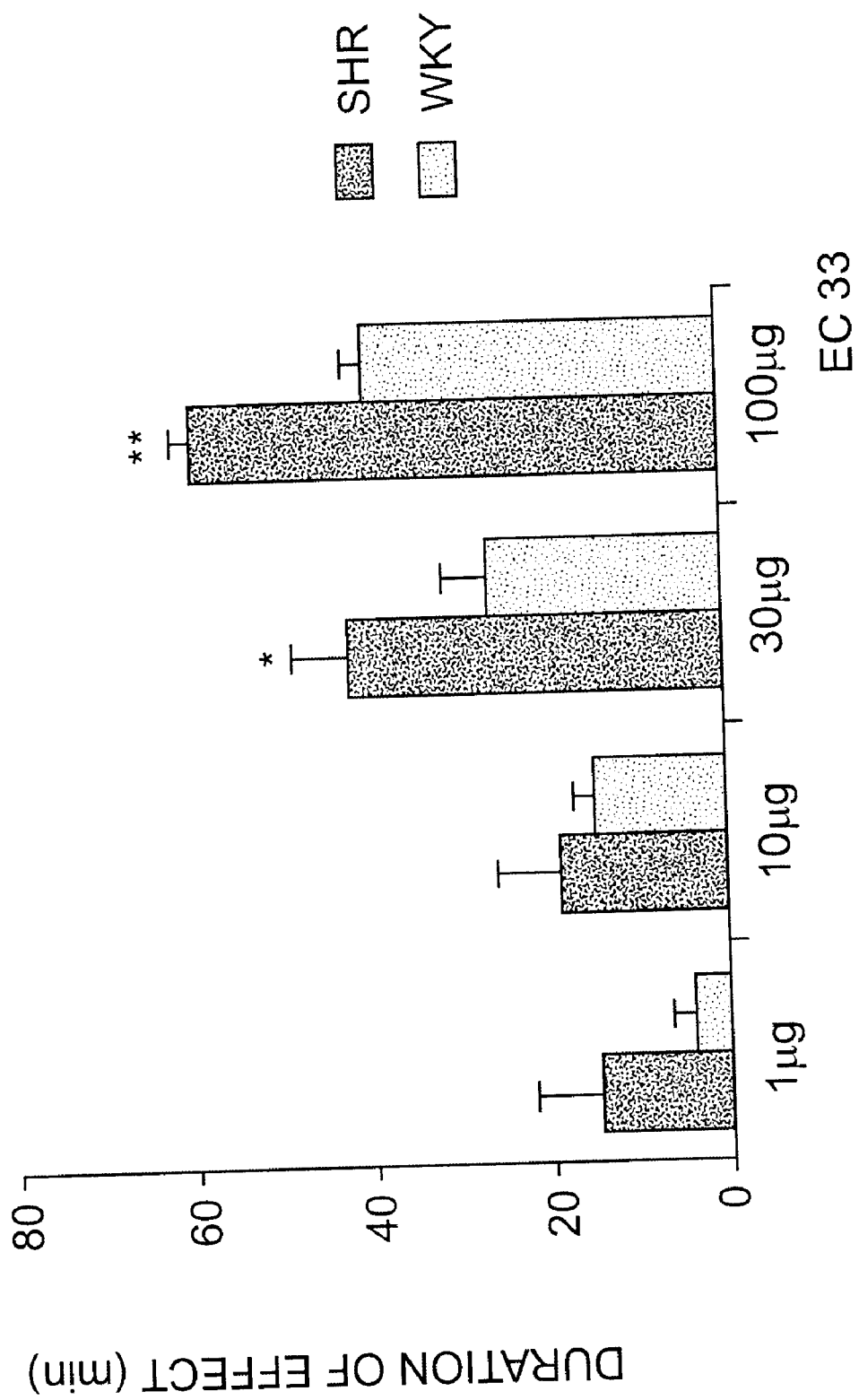

FIG. 4: Effect of various doses of EC33 in terms of duration of effect on arterial pressure in SHR and WKY rats.

Figure 5:
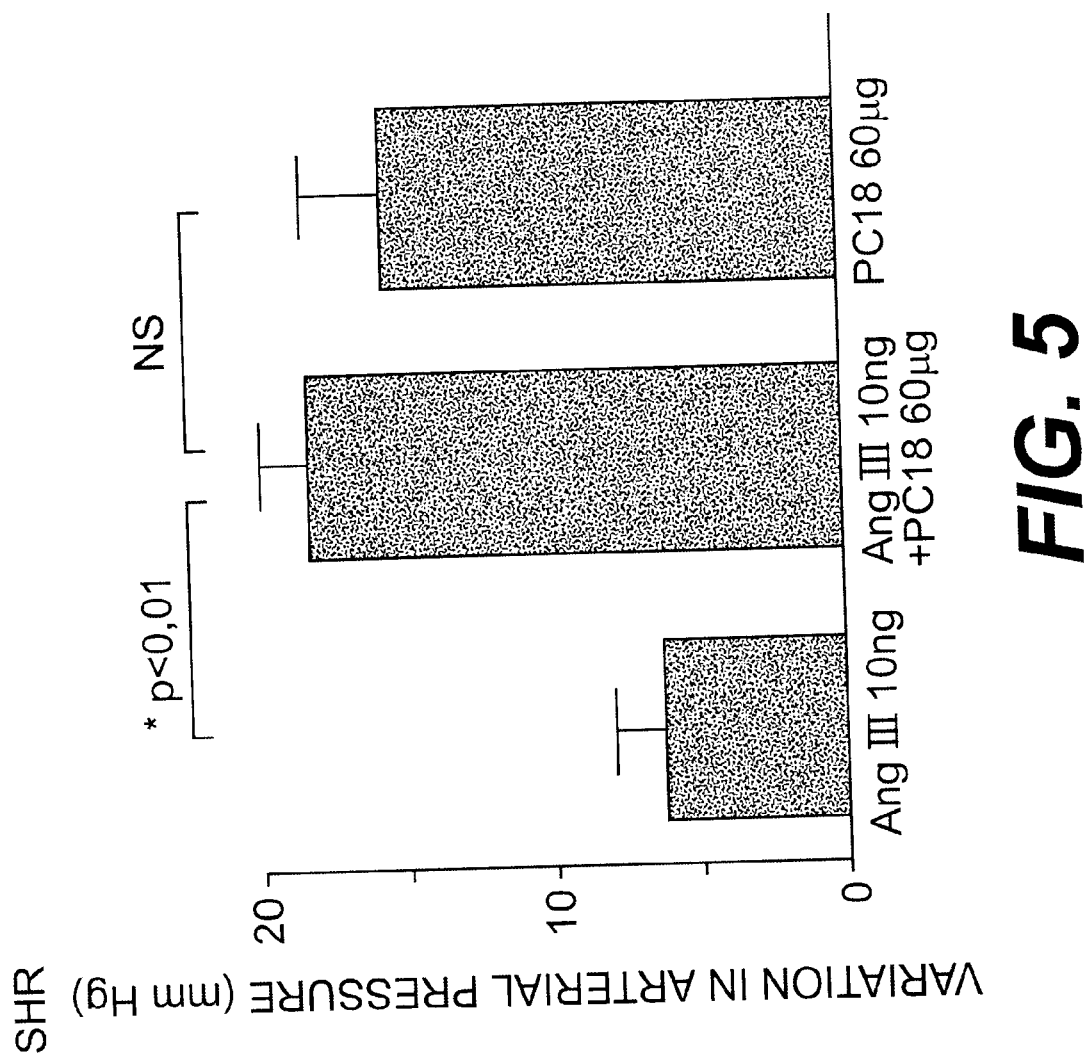

FIG. 5: Effect on pressure of an APN inhibitor, PC18, in SHR rats.

Figure 6:
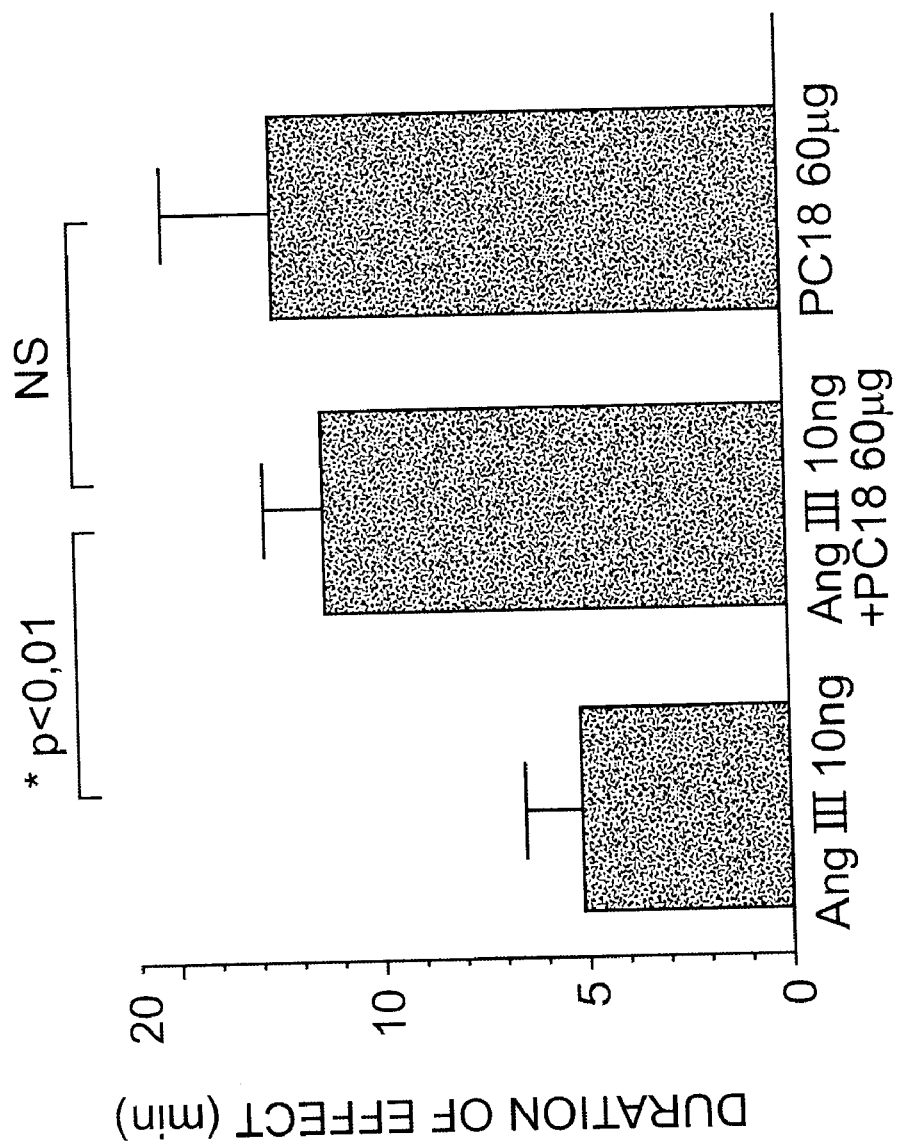

FIG. 6: Effect in terms of duration of an APN inhibitor, PC18, on arterial pressure in SHR rats.

Figure 7:
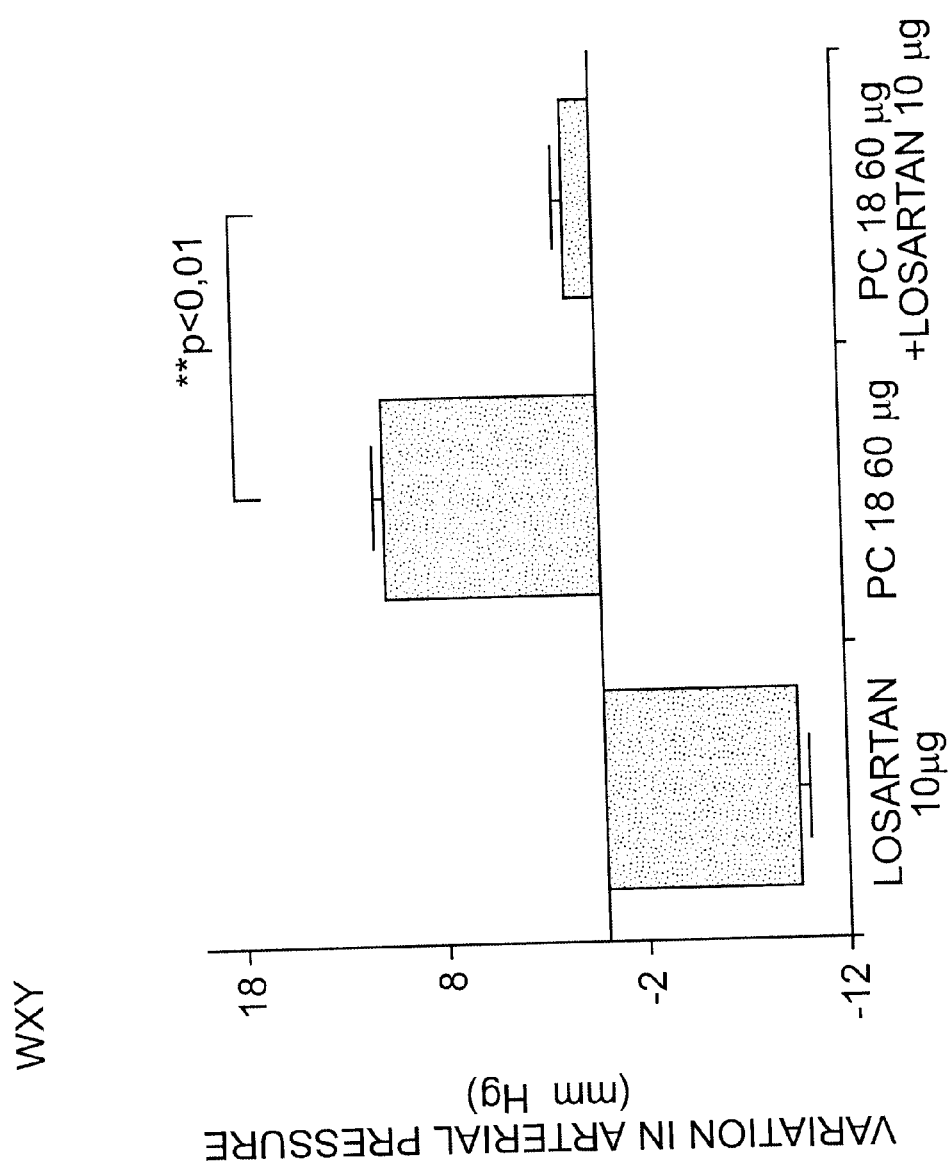

FIG. 7: Effect on pressure of an APN inhibitor, PC18, in normotensive rats in the presence of an antagonist of angiotensinergic receptors of type 1, AT1.

Figure 8:
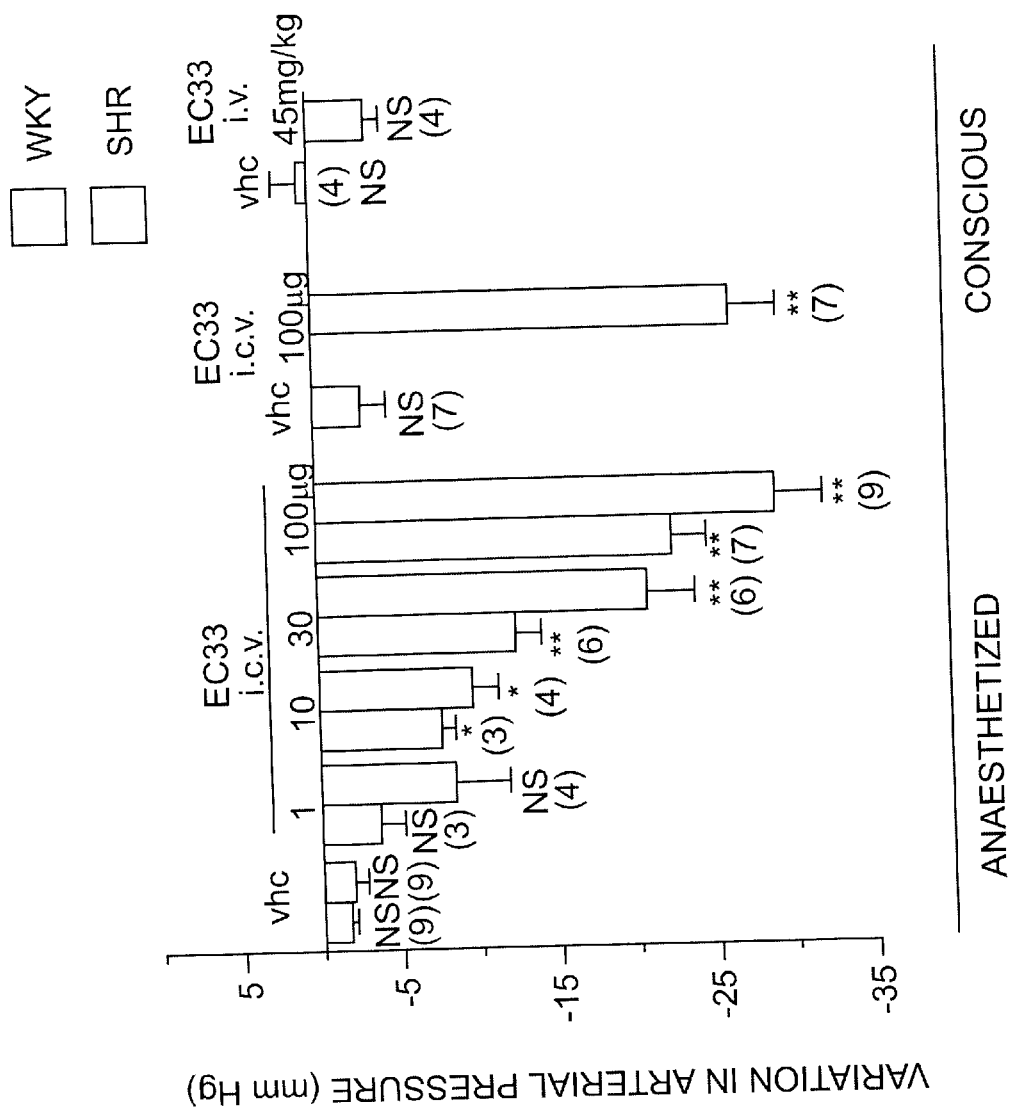

FIG. 8: Effect on arterial pressure of the inhibitor EC33 injected via the intracerebroventricular (i.c.v.) route or via the intravenous (i.v.) route in normotensive (WKY) or spontaneously hypertensive (SHR) conscious rats.

MATERIALS AND METHODS

A. Compounds

EC33, sodium (S)-3-amino-4-mercaptobutanesulphonate, is prepared according to the protocols described in Chauvel et al., J. Med. Chem. 37, 1339–1346 and 2950–2957.

PC 18, methioninethiol is a selective high affinity inhibitor for APN (Ki=9 nm). It is prepared according to the protocol described in Fournié-Zaluski et al., J. Med. Chem. 35, 1259-14 1266.

The various forms of angiotensin II and III considered below are available from the companies Amersham or Sigma.

B. Animals

Male Swiss mice (available from the IFFA Credo Institute) weighing 18 to 20 grams are maintained under artificial light (12 hours in bright phase - 12 hours in half-light) and have food and water available ad libitum. The experiments are carried out between 9 o'clock and 11 o'clock in the morning. The drugs are administered into the lateral ventricle by the intracerebroventricular route (i.c.v) at an amount of 5 µl per mouse according to the method of Haley and McCormick (Br. J. Pharmacol. 12, 12–15).

The rats used are male Sprague-Dawley rats weighing 200 to 250 grams; some of them are 11-week-old rats (SHR). Wistar Kyoto normotensive rats are also used as controls. The animals are kept for one week with alternating 12-hour periods of light and half-light, and have water and food available ad libitum. For each experiment, the SHR and WKY rats are weighed, and their arterial pressure and cardiac rhythm are continuously recorded via an invasive route after inserting a catheter (PE 50) into the femoral artery. The catheter is linked to a pressure sensor (COBE) and connected to a signal processor which is linked to an amplifier. The computer system comprises a MacLab interface system and application software (Chart and Scope) which allows data acquisition and calculation through a Macintosh computer.

C. Modes of Administration and Methods of Analysis

Intracerebroventricular Injection

For each experiment, six to eight mice are used for each of the conditions. A mixture of $2\times10^6$ cpm of [$^3$H]Ang II and 30 µg of unlabelled Ang II is administered in a 5 µl volume, alone or together with EC33 (30 µg). The inhibitors are dissolved in an isotonic saline solution adjusted to a pH of 7.4 with 0.01 M NaOH solution. At various times after the injection, the mice are decapitated, their brains are removed and their hypothalami are dissected on ice and homogenized by sonication (ultrasons, Anemasse, France) in 10 volumes of a 0.1 M HCl solution cooled in ice. The homogenate is centrifuged at 12,000×g for 20 min. at 4° C., and the supernatant is conserved at −8° C. until analysis.

Separation of Angiotensins II and III by Ion Exchange Chromatography

The respective amounts of labelled angiotensins II and III present in the hypothalamus are determined according to the protocol of Ledwith et al. (Anal. Biochem. 213, 349–355). To do this, a fast flow sepharose gel (½ dead volume, Pharmacia) is loaded into 3-ml syringe columns and equilibrated at room temperature with 15 ml of buffer (10 mM sodium acetate, 50 mM NaCl, pH 5.0). After having been thawed, the hypothalamus extracts containing approximately 30,000 cpm are diluted in 2 ml of equilibration buffer, loaded onto the columns and washed with 1 ml of buffer. A first fraction (F1) containing tritiated angiotensin II and other metabolites of tritiated angiotensin eluted with 7 ml of a solution of 10 mM sodium acetate/80 mM NaCl/5% acetonitrile at pH 5. A second fraction (F2) containing tritiated angiotensin III alone is eluted with 3 ml of a 3 M HCl solution. The F1 and F2 fractions are then analysed by HPLC to determine their respective content of tritiated angiotensin II and tritiated angiotensin III.

Concentration by Passing Over a $C_{18}$ Sep-pak® Column

With the aim of an HPLC analysis, the F1 and F2 fractions are initially concentrated by extraction on a $C_{18}$ Sep-pak® Cartridges device (Waters). For this, trifluoroacetic acid (1% at final concentration) is added to the F1 fraction, which is then loaded on to Sep-pak® preequilibrated with an aqueous 1% trifluoroacetic acid solution. The radioactive fraction is eluted with 1.5 ml of 100% acetonitrile. Under these conditions, 75% of angiotensin II is recovered. The F2 fraction is loaded on to Sep-pak® preequilibrated with 2 ml of a 100% methanol solution, followed by 5 ml of water. The radioactive fraction is eluted with 1.5 ml of 100% methanol. 92% of angiotensin III is thus recovered. After elution on Sep-pak®, the respective F1 and F2 fractions are freeze-dried, dissolved in 0.2 ml of a 0.01 M acetic acid solution, with 20 ng of angiotensin II and of angiotensin III as internal standard, and analysed by HPLC.

HPLC Analysis

The HPLC analysis is carried out using an H Hypersil ODS®-3 μm reverse phase column (Shandon, Pittsburgh) heated to 45° C., then with an isocratic elution at a flow rate of 0.6 ml per minute. The mobile phase consists of 86 mmolar $H_3PO_4$ adjusted to pH 3 with triethylamine, and of 17.5% acetonitrile. After injection of the sample (0.15 ml), 0.10 ml fractions are collected for 12 minutes. Their radioactivity content is estimated with a beta counter. Under such conditions, the retention times of the control angiotensins are 9.5 minutes for angiotensin II and 7.8 minutes for angiotensin III.

D. Measurement of APA Activity in Vitro

The assaying of the APA activity is based on the protocol of Goldbarg adjusted to the scale of assaying on microplates (Pro Bind™ 3915) (Chauvel et al., 1994).

Principle

In vitro, in the presence of calcium ions, APA hydrolyses α-L-glutamyl-β-naphthylamide (gluβNa) to glutamate and β-naphthylamine (βNa). A diazotation reaction in acid medium makes it possible to reveal the β-naphthylamine by formation of a violet-coloured complex: spectrophotometric measurement then makes it possible to know the amount of complex formed and, by reference to a standard curve produced with increasing concentrations of β-naphthylamine, to deduce therefrom the enzymatic activity of the sample.

Reagents

The GluβNa substrate and the β-naphthylamine (Bachem) are dissolved in DMSO (dimethyl sulphoxide) and 0.1 N HCl respectively, and conserved at −20° C. at a concentration of $10^{-2}$ M. The diazotation reaction is carried out in the presence of sodium nitrite (87 mM), ammonium sulphamate (130 mM) and N-(1-naphthyl)-ethylenediamine dihydrochloride (23 mM).

Enzymatic Reaction

The reaction takes place at pH 7.4 in 50 mM tris-HCl buffer, in the presence of calcium (4 mM $CaCl_2$); the sample to be assayed is incubated at 37° C. in the presence of substrate (200 μM GluβNa) and in the presence or absence of various concentrations of the inhibitor to be tested, in a final volume of 100 μl. The reaction is stopped by adding 10 μl of 3N HCl. A standard curve of β-naphthylamine in acid medium (add 10 μl of 0.1 N HCl) is produced in parallel.

Revelation of the Product Formed

The following are added to each well:

25 μl of sodium nitrite (mix, wait 5 minutes at room temperature),

50 μl of ammonium sulphamate (stir, wait 5 minutes at room temperature), then

25 μl of 23 mM N-(1-naphthyl) ethylenediamine dihydrochloride (mix, wait for stabilization of the violet colour, for approximately 30 minutes at 37° C.).

The absorbance is then measured at 540 nm.

E. Measurement of APN Activity

The assay principle is based on the hydrolysis of [$^3$H] Leu-encephalin (10 nM) by APN to two metabolites, [$^3$H] Tyr and the tetrapeptide Gly-Gly-Phe-Leu. Once the reaction has stopped, the [$^3$H] metabolite is isolated on a Porapak column, and its radioactivity is estimated by liquid scintillation. The activity of the APN is estimated in fmol of hydrolysed substrate/min/mg of protein.

F. Estimation of the Inhibitory Potency of EC33 and of PC18

The inhibitory potency of EC33 and of PC18 on APA or APN is estimated by measuring the enzymatic activity of purified APA or APN in the presence of increasing concentrations of the inhibitor. From these data, the effective concentration 50 is calculated according to a least squares nonlinear regression program (Graph Pad PRISM™, version 2), which makes it possible to deduce the KI of these molecules according to the following formula:

$$KI = \frac{IC50}{1 + \frac{Km}{[S]}}$$

The Km of APA for GluβNa is 100 μM (Vazeux et al., J. Biochem., 1966, Vol. 271: 9069–9074).

The Km of APN for Leu-encephalin is 50 μM (Chauvel et al., J. Med. Chem., 1994, Vol. 37: 2950–2956).

Example 1

In Vitro Assay of the Inhibitory Potency of EC33 and of PC18 on APA and APN

These inhibitory potencies are estimated in accordance with the protocol described in the "materials and methods" chapter.

EC33 has a KI of $2.5 \pm 0.6 \times 10^{-7}$ M for APA and a selectivity factor of approximately 100 with respect to APN ($25 \pm 11 \times 10^{-6}$ M).

The inhibitory potency of PC18 on APN is $1.1 \pm 0.1 \times 10^{-8}$ M, and it is 1000 times less active on APA ($11 \pm 1.7 \times 10^{-6}$ M).

Example 2

In Vivo Effect of the Inhibitor EC33 on the Metabolism of the Cerebral Angiotensins AngII and AngIII Present in the Murine Hypothalamus The kinetics of appearance and of disappearance in the hypothalamus of the radiolabelled angiotensins II and III are determined after having injected into mice, via the intracerebroventricular route, a known amount of tritiated AngII ($2 \times 10^6$ cpm) with 30 μg of nonradioactive (EC33, 30 μg). The levels of the tritiated peptides in the tissues are quantified by HPLC according to the protocol described in the "materials and methods" chapter.

The evolution of the [$^3$H] AngII content in the hypothalamus after i.c.v. injection of [$^3$H] AngII in the presence or absence of EC33 is reported in FIG. 1.

In control mice, the [$^3$H] AngII content decreases rapidly after 1.5 minutes and is no longer detectable beyond 7 minutes. In the presence of EC33, this [$^3$H] AngII content is significantly increased between 0.5 and 7 minutes so as to reach approximately 11 times the content of the control test.

A semi-logarithmic representation of the rate of disappearance of [$^3$H] AngII content in the presence of EC33 with respect to the control is presented in FIG. 2.

It is noted that in animals treated with EC33, the half-life of the [$^3$H] AngII ($5.38 \pm 0.21$ min) is increased by a factor of 2.6 compared to that of a control animal.

In control mice, the formation of tritiated AngIII is at a maximum at 1 minute, and the levels decrease gradually up to 10 minutes. In the presence of EC33, the formation of tritiated AngIII is immediately blocked, and very low levels are measured throughout the experiment.

Example 3

In Vivo Effect of the Inhibitor EC33 on an ANGII-Induced Increase in Arterial Pressure.

These experiments are carried out in Wistar Kyoto (WKY) normotensive rats or spontaneously hypertensive rats (SHR 12 weeks old).

The animals are anaesthetized with Inactin (5-ethyl-2-(1'-methylpropyl)-2-thiobarbita), this being an anaesthetic which is used regularly in renal or cardiovascular physiology experiments. Its properties are to cause a very slight drop in arterial pressure, which is visible only in SHR rats, and especially to allow a stable basal arterial pressure to be maintained throughout the experiment.

The mean arterial pressure (systolic+diastolic) is measured continuously, via an invasive route, after catheterizing the femoral artery. The peptides or the inhibitors, are injected via the intracerebroventricular (i.c.v.) route with the aid of a cannula positioned in the lateral ventricle under stereotaxy (Stereotaxic Atlas; G. Paxinos and C. Watson, Academic Press, 1986).

The experiments are carried out on groups of 4 to 20 individually analysed animals. The results on batches of control animals and treated animals were compared with the aid of an analysis of variance (ANOVA), followed by an unpaired Student's test.

An injection of angiotensin II is carried out combined, where appropriate, with a consecutive injection of EC33.

The tests are carried out according to the schemes below which report the results obtained.

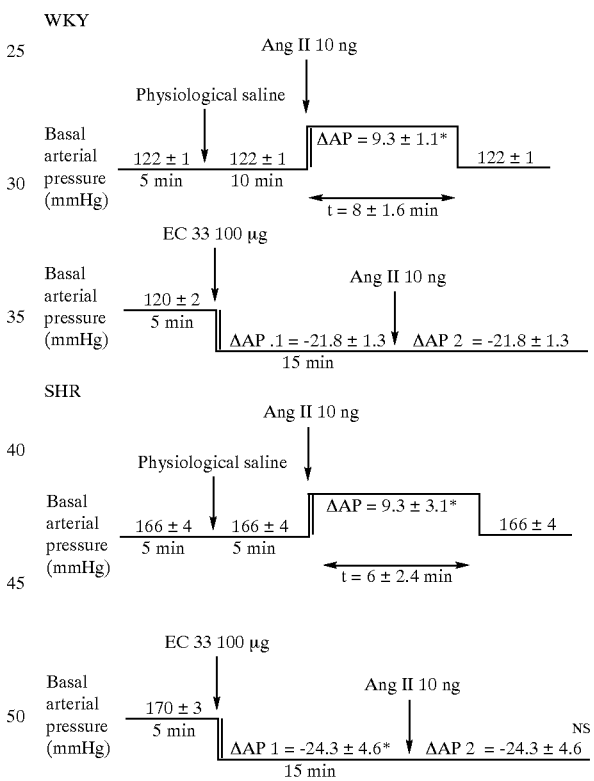

It is noted that ANGII at a dose of 10 ng significantly increases arterial pressure (AP). This effect is slightly greater in SHR rats than in WKY rats. The maximum magnitude of the effect is approximately 10 mmHg for 10 ng of AngII, and the duration of action is between 7 and 9 minutes.

When the AngII (10 ng) is injected in the presence of 100 μg of the aminopeptidase A inhibitor, EC33, the effect on pressure of the AngII is completely eliminated.

The specificity of action of EC33 was also demonstrated through its ineffectiveness in modifying the effect on pressure of the AngIII (30 ng). The schemes which are shown below report the results obtained.

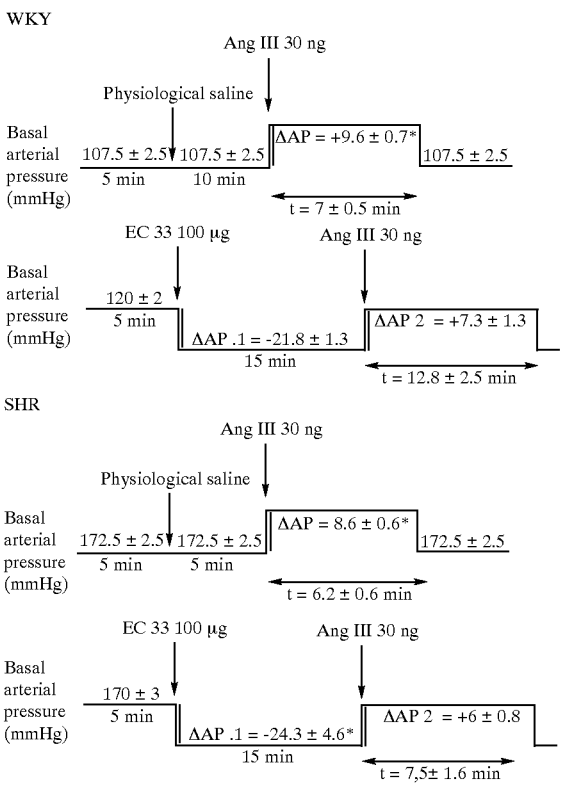

The dose-dependent effect of EC33 injected alone was also assessed in terms of duration of action and hypotensive effect. The results obtained are represented in FIGS. 3 and 4.

In general, when APA is blocked by EC33, a dose-dependent drop in AP is observed, this being more marked in hypertensive rats than in normotensive rats. The hypotensive effect of the APA inhibitor is at a maximum for a dose of 100 µg. It is −22 mmHg in normotensive rats and −28 mmHg in hypertensive rats.

The duration of action at this dose is on average between 40 and 60 minutes.

Consequently, these data indicate that, under the basal conditions, endogenous angiotensin III exerts a positive tonic effect on the central control of arterial pressure.

Example 4

Demonstration of the Determining Role of AngIII in the Cerebral Renin/Angiotensin System This test is carried out with the aid of an aminopeptidase N (APN) inhibitor, PC18(3-amino-4mercaptomethionine). This APN is responsible for the degradation of angiotensin III to angiotensin IV.

In accordance with the protocol described in Example 3, AngIII (10 ng) in the presence of 60 µg of PC18 is injected into SHR rats. As a control test, an injection of PC18 alone is carried out.

The effect of this co-injection is assessed in terms of arterial pressure and of duration, and the results obtained are present in FIGS. 5 and 6.

A potentiation of the effect on pressure of AngIII (10 ng) is observed on taking the inhibitor PC18 (60 µg). At 60 µg, PC18 alone increases arterial pressure by 50 mmHg in SHR rats, and the effect lasts approximately 12 minutes.

Moreover, it has also been shown, in normotensive or hypertensive rats, that the increase in arterial pressure (+10 or +13 mmHg, respectively) induced by 60 µg of PC18 is antagonized by a pretreatment with an antagonist of angiotensinergic receptors of type 1 (AT1), Losartan (10 µg). This is in particular illustrated in FIG. 7 for normotensive rats.

This antagonist effect is about 85% in normotensive rats and about 52% in hypertensive rats.

From these data, it emerges that the effect on pressure of PC18 is due to an accumulation of endogenous AngIII through the AT1 receptors.

Example 5

Effect on Arterial Pressure of the Inhibitor EC33 Injected Via the Intracerebroventricular (i.c.v.) Route or Via the Intravenous (i.v.) Route in Conscious Rats These experiments are carried out in a 12-week-old SHR rats (300–350 g). During the operation, the animals are anaesthetized for a limited time (3 hours) with sodium pentobarbital (50 mg/kg intraperitoneal, Laboratoire Sentravet, Plancoët, France) The experiments are carried out a minimum of 24 hours after the operation.

Injection via the i.c.v. route.

The injections are carried out with the aid of a cannula positioned in the lateral ventricle under stereotaxy, and the arterial pressure is measured continuously, via an invasive route, after catheterizing the femoral artery. The catheter is exteriorized at the level of the animal's neck, and is linked to a fixing system which allows the rat to move around freely in its cage.

Injection via the i.v. route.

A first catheter is positioned in the femoral vein in order to carry out the injections, a second catheter is introduced into the femoral artery in order to be able to measure arterial pressure continuously. Both catheters are then exteriorized as indicated above.

The results obtained are represented in FIG. 8.

It is noted that, in the conscious SHR rats, the i.c.v. injection of EC33 at a dose of 100 µg significantly decrease the arterial pressure (−26 mmHg) about the same as in the anaesthetized animals (−28 mmHg). (FIG. b). This hypotensive effect does not, however, last as long (40 min).

Conversely, when injected via the i.v. route, EC33 at a dose of 45 mg/kg does not induce a significant hypotensive effect in the conscious SHR rats (FIG. c).

These results thus show that endogenous cerebral AngIII exerts a tonic action in the regulation of arterial pressure both in anaesthetized rats and in conscious rats. The results obtained peripherally show that blocking the conversion of circulating AngII into AngIII does not induce any significant modification of arterial pressure.

This suggests that cerebral APA plays a predominant role in regulating arterial pressure compared with peripheral APA which appears to have a lesser contribution.

What is claimed is:

1. Pharmaceutical composition useful for decreasing arterial pressure, comprising as an active principle, at least one selective aminopeptidase A inhibitor.

2. Composition according to claim 1, wherein the inhibitor has an affinity which is multiplied by at least a factor of 100 for aminopeptidase A compared to aminopeptidase N.

3. Composition according to claim 1 wherein the inhibitor is (S)-3-amino-4-mercaptobutylsulphonic acid or a salt thereof with a pharmaceutically acceptable acid or base.

4. Composition according to claim 1 which, claim 1 which it also comprises at least one pharmaceutically acceptable vehicle.

5. Composition according to one of the preceding claims, characterized in that it also comprises an angiotensin I converting enzyme inhibitor or an antagonist of AT1 receptors.

6. Method for decreasing arterial pressure comprising administering an effective amount of an aminopeptidase A inhibitor as defined in claim 1 in combination, where appropriate, with a pharmaceutically acceptable vehicle to a patient in need of such treatment.

7. The pharmaceutical composition of claim 1, wherein said aminopeptidase A inhibitor is in a form which can cross the blood brain barrier.

8. The method a according to claim 6, wherein the aminopeptidase A inhibitor is in a form which can cross the blood brain barrier.

9. A method for decreasing arterial pressure comprising administering an effective amount of aminopeptidase A inhibitor that crosses the blood brain barrier, in combination where appropriate, with a pharmacologically acceptable vehicle to a patient in need of a such treatment.

10. The method according to claim 9, wherein the aminopeptidase A inhibitor in a form which does not cross the blood brain barrier by injecting the aminopeptidase inhibitor directly via the intracerebroventricular route.

11. The method according to claim 9, wherein the aminopeptidase A inhibitor is in a form which can cross the blood brain barrier whereby the aminopeptidase A inhibitor crosses the blood brain barrier via the systemic root.

12. The method for decreasing arterial pressure comprising administering an effective amount of an aminopeptidase A inhibitor as defined in claim 2 in combination, where appropriate, with a pharmaceutically acceptable vehicle to a patient in need of a such treatment.

13. The method for decreasing arterial pressure comprising administering an effective amount of an aminopeptidase A inhibitor as defined in claim 3 in combination, where appropriate, with a pharmaceutically acceptable vehicle to a patient in need of such a treatment.

14. The method for decreasing arterial pressure comprising administering an effective amount of an aminopeptidase A inhibitor as defined in claim 5 in combination, where appropriate, with a pharmaceutically acceptable vehicle to a patient in need of a such treatment.

* * * * *